Figure 1:
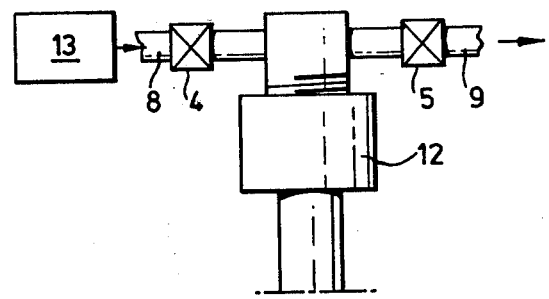

United States Patent [19]
Knox

[11] 3,981,801
[45] Sept. 21, 1976

[54] GRADIENT STORAGE METHOD FOR LIQUID CHROMATOGRAPHY

[75] Inventor: John Henderson Knox, Edinburgh, Scotland

[73] Assignee: University of Edinburgh, Edinburgh, Scotland

[22] Filed: Feb. 14, 1974

[21] Appl. No.: 442,583

[30] Foreign Application Priority Data
Feb. 14, 1973 United Kingdom............. 7142/73

[52] U.S. Cl. ..................... 210/31 C; 210/198 C
[51] Int. Cl.² ............................. B01C 15/08
[58] Field of Search .................. 210/31 C, 198 C

[56] References Cited
UNITED STATES PATENTS

| | | | |
|---|---|---|---|
| 3,373,872 | 3/1968 | Hadina | 210/198 C |
| 3,504,799 | 4/1970 | Ogle | 210/198 C |
| 3,575,295 | 4/1971 | Yoshida | 210/198 C |
| 3,578,785 | 5/1971 | Patterson | 210/198 C |
| 3,583,230 | 6/1971 | Patterson | 210/198 C X |
| 3,826,373 | 7/1974 | Andreotti | 210/198 C |

*Primary Examiner*—John Adee
*Attorney, Agent, or Firm*—Brisebois & Kruger

[57] ABSTRACT

A method of preparing samples of a liquid the composition of which varies from one region to another within a given volume, for subsequent storage or use, in which a first liquid is introduced into a long narrow tube which has particular dimensions and which may or may not be provided with a particulate filling, and subsequently a second liquid is introduced into the tube in circumstances such that in the tube the second liquid has a varying composition from point to point along the tube. The variation in composition may be caused by absorption by a packing if the tube has one, by dispersion of the front between the first and second liquids if they are miscible, or the second liquid may already have such a variable composition when introduced into the tube. The ends of the tube are then sealed if the sample is to be stored.

9 Claims, 2 Drawing Figures

U.S. Patent   Sept. 21, 1976   3,981,801

GRADIENT STORAGE METHOD FOR LIQUID CHROMATOGRAPHY

The present invention relates to a method of preparing samples of a liquid the composition of which varies from one region to another within a given volume, and in particular to a method for use in connection with the technique known as gradient elution or solvent programming as applied in liquid chromatography and especially in high speed liquid chromatography.

The invention also relates to apparatus for use in the method.

It has been proposed to employ as eluent in liquid chromatography a liquid whose composition is changed either continuously or stepwise during the elution process in order to bring about the elution in a short time of different solutes possessing between them a wide range of affinities for the stationary phase within the chromatographic column. In high speed liquid chromatography the eluent is commonly fed to the column at a pressure which may be as high as 300 atm by means of a pressurisation system which may comprises for example, a reciprocating pump, a pressure intensifier, or a motorised syringe. Existing arrangements for producing changes in the composition of the solvent entering the chromatographic column are of two types, both of which mix liquids to produce the necessary changes of composition; the first type effects mixing before, that is upstream of, the pressurization system, and the second type effects mixing after, that is downstream of, the pressurization system. The first type of arrangement requires close attention to be paid to the geometry of the volume of the system between the mixing point and the column inlet; for example, this volume must be well flushed and made as small as possible. These requirements are difficult to meet since this volume must include the working spaces of the pressurization device, an anti-surge device and pressure measuring device. The second type of arrangement demands the long term operation of one or more programmable valves which mix liquids to the necessary changing composition under high pressure conditions. Both of these arrangements are difficult to engineer, and have disadvantages in practice, particularly when used in high speed, high pressure liquid chromatography.

According to one aspect of the present invention a method of preparing samples of a liquid the composition of which varies from one region to another within a given volume, for subsequent discharge to chromatographic or other apparatus comprises the steps of connecting to a source of a first liquid an elongate tube the dimensions of which are such that any given band of solution passed along the length of the tube and surrounded by a liquid of given different composition will always be dispersed to the same extent, filling the available space in the tube with the said first liquid, subsequently replacing at least part of the said first liquid in the tube with a sample volume of a second liquid the composition of which varies along the length of the tube in a predetermined manner, and closing off both ends of the tube to seal in the sample volume of the said second liquid.

Preferably the method also includes the step of filling the tube with a particulate material such as glass beads.

Apparatus for carrying out the method of the invention constitutes a further aspect of the present invention.

According to this further aspect of the invention apparatus for preparing samples of a liquid the composition of which varies from one region to another within given volume, by a method as defined above comprises an elongate tube the dimensions of which are such that any given band of solution passed along the full length of the tube and surrounded by a liquid of given different composition will always be dispersed to the same extent, means for introducing a first liquid into the tube, means for introducing a sample liquid into the tube by displacing the said first liquid such that the composition of the sample liquid varies from one region to another along the tube, and means for sealing the ends of the said tube.

The invention also comprehends a method of performing chromatographic analysis using samples prepared as defined above.

Figure 2:
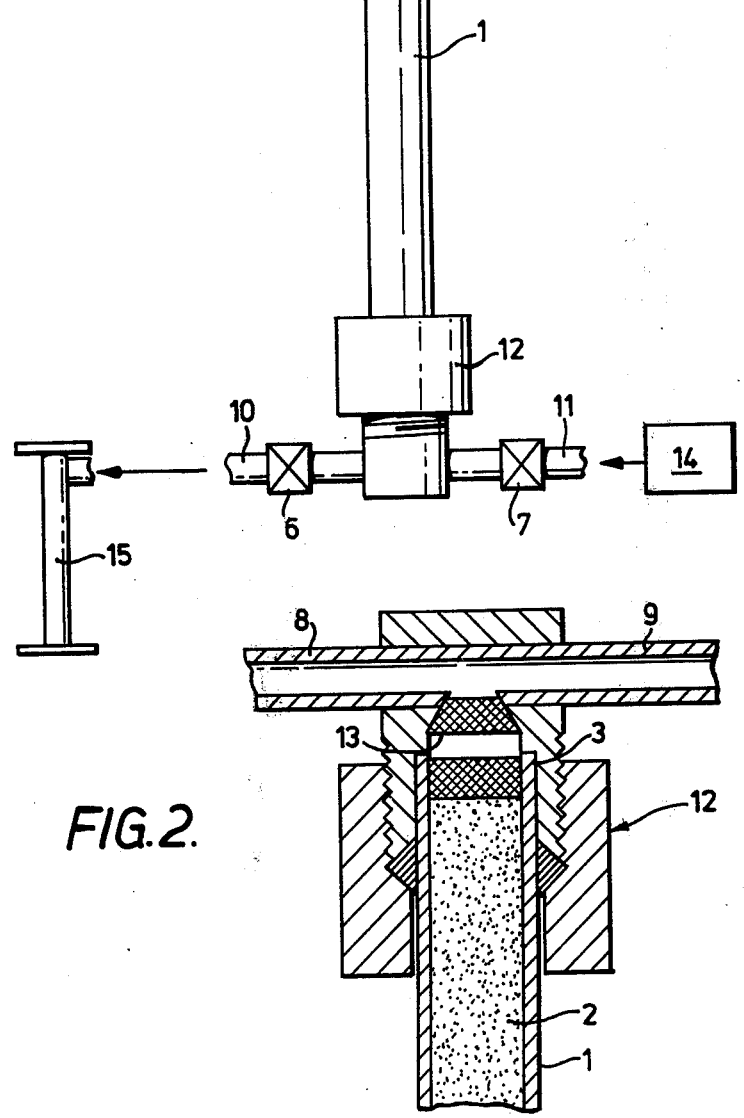

The invention will now be further described, by way of example with reference to the accompanying drawing, in which:

FIG. 1 is a schematic view of the embodiment of apparatus for carrying out the method of the invention, and FIG. 2 is a sectional elevation of part of the apparatus of FIG. 1, shown on an enlarged scale.

Referring now to FIG. 1, a stainless steel tube, 1 of internal diameter between 3 and 15 mm and with walls of sufficient thickness to withstand a pressure of up to 300 atm gauge, and of sufficient length to contain between 10 and 100 cm$^3$ of liquid, is filled with glass beads 2 (of. FIG. 2) with a mean particle diameter of between 0.05 and 0.2 mm, the beads being retained in the tube by means of porous frits 3 at each end of the tube, and is connected at each end to respective pairs of single channel valves 4, 5 and 6, 7, of small internal volume by means of narrow bore tubes, 8, 9 and 10, 11 the bore diameter of which is about 0.5 mm.

The tubes 8–10 are themselves connected to inlet/outlet units 12 attached to the tube 1 and which are so designed as to give smooth streamline flow throughout their internal volume and to have only small internal volumes so that the stagnant liquid contained thereby during the filling procedure is minimised. A design for an inlet/outlet unit 12 which has been found satisfactory is shown in FIG. 2. This is basically a "Swagelok S10-C" fitting clamped around the end of the tube 1 and connecting to a continuous small bore tube 8/9. A flow improver frit 13 is located in the fitting, and a glass bead retaining frit 3 is located in the end of the tube 1.

In place of the single channel valves 4–7, one or more multichannel valves may be used to provide the same function as the four single channel valves, and may be used with good effect provided that their internal volumes and those of any connecting tubes are low.

To employ the illustrated equipment in the method of the invention, the tube 1 is initially filled with a solvent from an external pressurization device 13 which is typically part of a high speed liquid chromatographic system and is connected to the tube 8 by opening valves 4 and 6, care being taken to displace all the air or other fluid from the tube 1. The tube 10 is at this time connected to allow liquid flowing therethrough to flow into a discharge vessel (not shown). Valves 4 and 6 are then closed and valves 5 and 7 are opened. A mixture with the desired varying composition is next pumped from a low pressure gradient producing device 14 connected to the tube 11 so as to enter the tube at valve 7, and for example this may be simply achieved by the use of a syringe which is successively filled with small portions of solutions of slightly differing composition, these successive small portions being injected sequentially into the tube 11 through a penetrable wall portion thereof. The addition of the liquid of varying composition through the valve 7 displaces all or part of the liquid already contained in the tube 1 through the valve 5 (where it can flow through the tube 9 to waste), and so fills or partially fills the tube 1 with the liquid of varying composition. It is arranged that the mixture first entering the tube 1 is miscible with the liquid subsequently to be delivered by the pressurization system 13, and that the liquid last entering the tube 1 is miscible with the liquid contained within the chromatographic column 15 which is connectable to the tube 10, and has a composition which is suitable for the start of the gradient elution programme. Valves 5 and 7 are then closed so that the mixture of variable composition is stored in the tube 1. Because of the slow rate of mixing by molecular diffusion of static liquids within the packed tube 1, the mixture may be stored without significant change in its composition from zone to zone for several hours. By opening valves 4 and 6 and connecting the tube 10 to the inlet of the chromatographic column 15 the liquid of varying composition can then be fed via the tube 10, to the chromatographic column 15.

As an alternative, the mixture of variable composition may be fed to the tube 1 via valve 5 instead of via valve 7.

The purpose of the packing and of the dimensions suggested is to ensure that the composition variation within the liquid fed from the tube 1 to a chromatographic column is reproducibly related to the composition of the liquid originally fed to the storage tube 1. This is most readily achieved if the dimensions are so arranged that an initially sharp band (or front) of solution whose composition differs slightly from that already fed to the tube 1 is not greatly dispersed by passage along the complete length of the tube, and in this connection a dispersion amounting to not more than one third of the length of the tube would be satisfactory, but the specification of such a desirable upper limit of dispersion should not be construed as a limitation of the invention which can equally well be applied where the dispersion is larger but reproducible.

Thus according to prior art well known to those skilled in chromatography, when an initially sharp band of liquid whose composition differs slightly from that of the surrounding liquid, or when a liquid with a composition suddenly different from that previously fed to the tube (that is a front) is passed into a tube containing 0.10 mm diameter glass beads at a linear speed of 0.1 cm per second, the initially sharp band (or front) will be dispersed to give a diffused band (or front) about 3 cm (or about 2.4 cm in the case of a front) in width when the band (or front) has traversed 20 cm of the length of the tube, and in general the width of the band (or front) will obey one or other of the following equations relating respectively to band width and front width:

$$W = 4(HZ) \tag{3}$$

$$W = (\pi HZ) \tag{2}$$

where:

$H$ is a constant called the height equivalent to a theoretical plate, and $Z$ is the distance migrated by the band (or front).

In the present example $H$ may be about 0.3 mm.

In order to ensure that the desired compostion variation is reproducibly delivered by the equipment it is important that the orientation of the tube 1 in space is chosen so as to minimize the effects of density differences which could lead to undesirable convection effects and to irreproducibility in the composition variation of the liquid finally delivered to the chromatographic apparatus (or other equipment). For example, it is preferable that the tube 1 be mounted vertically where possible with the inlet valves 6 and 7 at the bottom if the first liquid to be fed to the tube from the gradient producing device through the valve 7 is the least dense. The tube should preferably be mounted in a temperature controlled environment to minimize the effects of thermal convection, and additionally, for its use in chromatography, it is important to maintain the liquid contained in the tube 1 at the same temperature as the chromatographic column eventually to be supplied with the liquid therein contained.

In place of glass beads 2 for the packing of the tube 1, particles of kieselguhr, silica gel, ground pumice, polymer beads or other particulate fragments of comparable size range can be used.

Alternatively an open tube of small bore diameter may be used for the storage of the liquid of variable composition, and for example, a tube 70 m in length, 0.6 mm in diameter and having a volume of 20 cm$^3$ wound into a helix of say 10 cm diameter is satisfactory. It has been found that when a band or front (as previously described in connection with the use of a packed tube) is passed into a straight open tube of radius $r$ for a time $t$, and when the diffusion coefficient of the molecules of the band (or liquid behind the front) in the adjacent liquid is $D$, then the fraction, $F$, of the length of the tube traversed which is occupied by the dispersed band (or front) after the time, $t$, is given by the following equations for a band or a front, respectively, $$F = r/(1.5Dt) \tag{3}$$

$$F = r/(3.8Dt) \tag{4}$$

Furthermore if $t$ is taken as the time for the band, or front, to reach the end of the tube, and $V$ is the total volume of the tube, the pressure required to drive the band or front along the completely filled tube at a constant rate is given by:

$$P = (0.24 \ V^2 \eta)/(F^6 D^3 t^4) \tag{5}$$

the viscosity of the liquid being $\eta$. For the conditions of the above example using water as the liquid, $F$ would be about ⅓ for a band or 1/5 for a front when the filling time was 8 minutes. The required pressure drop would then be about 10 atm. From the second formula it is clear that smaller values of $F$ would be difficult to attain without either undue pressure penalty or considerable extension of the filling time. It is therefore evident that the open tubular version of the invention is less desirable than the pack-tube version if it is desired that the composition variation of the liquid fed to the chromatographic column (or other equipment) is to be a faithful reproduction of that initially fed to the storage tube.

However, the property of a tube to disperse a band or front in a reproducible manner may itself be advantageously employed in the generation of a liquid of smoothly varying composition throughout its volume starting from a liquid where composition changes in a stepwise manner. For example if a tube of diameter 0.8 mm and of 20 m³ volume is first filled with a liquid A, and then a liquid B, miscible with A, is passed into the tube so that in a time of 100 sec the calculated position of the front between A and B if assumed to remain undispersed would be exactly half way along the tube, the front will in fact be found to be dispersed so as to occupy a total distance equal to a quarter of the length of the tube on either side of the calculated position of the, assumed undispersed, front. The initially sharp front has thereby been converted into a dispersed front within which the composition of the liquid varies in a controlled way. Although the range of profiles of the variation of composition of the liquid generated in this way is limited, the simplicity of the method of generation of a reproducible variation in composition may outweigh the disadvantage in certain applications. The steepness of the variation of composition in the dispersed front is easily controlled by control of the filling time as seen from equations 3 and 4.

The open tubular storage tube is used in the same way as the packed storage tube in all respects except that the liquid first fed to the tube need not necessarily be miscible with the liquid to be delivered by the pressurization system: indeed it may in certain applications be advantageous if these two liquids are immiscible.

Alternatively an open tube may be combined with a packed tube to form the storage unit, and for example the part of the storage unit nearest to the valve 4 connected to the pressurization system may be void while the part connected to the gradient forming system via the valve 7 is packed. It is then possible to employ a liquid in the pressurization system which is immiscible with liquid originally contained in the packed part of the storage tube, provided that care is taken that the equipment is mounted in such a way that the denser of the two immiscible liquids is in the lower part of the open tubular part of the storage unit.

After completion of the elution of a sample through the chromatographic column by the mixture of varying composition it may be foound necessary to regenerate the chromatographic column packing by passing through it a liquid whose composition is changed in a sequence which is the reverse of that of the mixture originally fed to the column. This regeneration procedure may be carried out using the storage tube in precisely the same way as for the original mixture except that the tube is now filled with a solution whose composition follows a reverse sequence of composition changes with respect to that originally employed. Alternatively, a second gradient storage tube with its own system of valves essentially identical to the first, may be used in parallel with the first. A cyclic program is thus possible in which the first tube is filled with the mixture of variable composition required for regeneration of the column, while the sample is eluted through the chromatographic column by passage of the mixture of variable composition required for elution which has been stored in the second tube. Following elution, the solvent of variable composition required for regeneration is passed to the column, while the second tube is refilled with the solvent of variable composition required for elution.

Alternatively, the gradient storage tube may be packed with an adsorbent such as silica gel and a mixed solvent of constant composition passed into the tube 1 through the valve 5 instead of the valve 7 so that the sample passes right through the tube 1 when fed out through valve 6 to a chromatographic column or other apparatus. Preferential adsorption of the more polar components of the mixed solvent from that part of the mixed solvent first entering the tube 1 will then produce a composition gradient within the tube. After passage of the solution of variable composition to the chromatographic column, the activity of the packing in the storage tube 1 may be regenerated by the passage of a solvent of low polarity through the storage tube which can then be reused to give a mixture whose composition varies throughout its volume in a reproducible manner.

What is claimed is:

1. A process for the preparation, storage and subsequent pressurized delivery of a sample liquid whose composition varies in a reproducible and controllable way from one region of its volume to another, comprising filling an elongate tube with a first liquid, the geometrical dimensions of said tube being chosen so that a sharply defined band of one liquid whose composition differs from that of a surrounding liquid is dispersed in a reproducible way when said band is passed at a specified rate through said tube, subsequently introducing into said tube a second liquid miscible with said first liquid so as to displace at least part of said first liquid, the composition of the second liquid being controlled during the introduction procedure according to a prearranged programme to effect a predetermined dispersion of said second liquid which forms a precursor sample, closing at least one end of said tube to hold and store said precursor sample within said tube, and subsequently expelling said precursor sample at the outlet of said tube into pressurized equipment to form the sample liquid whose composition varies in a reproducible and controlled manner from one region of its volume to another.

2. A process as claimed in claim 1 in which the dimensions of the elongate tube are chosen so that any initially sharp band of liquid of negligible width when passed through the length of the tube in a time not exceeding 200 seconds is dispersed to an extent not exceeding one half of the total length of the tube.

3. A process as claimed in claim 1 in which said elongate tube has an internal diameter of 0.2 to 1 mm and is of sufficient length to contain between 10 and 100 cm³ of liquid.

4. A process as claimed in claim 1 in which said tube is pressurized up to 300 bar during delivery of the sample liquid from the tube outlet.

5. A process as claimed in claim 1 in which said elongate tube is packed with a particulate material, the dimensions of the particulate material being among those selected so that a sharply defined band of one liquid whose composition differs from that of a surrounding liquid is dispersed in a reproducible way when said band is passed at a specified rate through the tube packed with the particulate material.

6. A process as claimed in claim 5 in which the storage tube has an internal diameter between 3 and 15 mm and is of sufficient length to contain between 10 and 100 cm³ of liquid, and in which said particulate material is chosen from the group consisting of glass beads, porous glass beads, silica gel beads, silica gel chips and fused diatomaceous earth and whose mean particle size is between 0.02 and 0.2 mm, said particulate material being retained within said tube by a liquid permeable barrier.

7. A process as claimed in claim 1 carried out in a tube fitted with two valves at each end, said process comprising the steps of connecting said tube, via the said valves respectively to a first line leading from a high pressure chromatographic pump, to a second line leading to a chromatographic column at the opposite end of the tube to the said first line, to a third line leading from equipment used to prepare said second liquid and to a fourth line for drainage at the opposite end of the tube to the said third line, first closing the valves to said first and second lines while the valves to said third and fourth lines are opened while the said second liquid is fed into said tube displacing said first liquid, and subsequently closing the valves of the third and fourth lines while the valves to the first and second lines are opened to pass said sample liquid from the tube into the chromatographic column.

8. A process as claimed in claim 1 in which the composition of the second liquid differs from the desired sample liquid to allow for dispersions resulting from the act of introduction of said second liquid and the delivery of said sample liquid from the tube.

9. A process as claimed in claim 1, in which two storage tubes are employed, the first containing a liquid whose variation of composition over its length will, on discharge from the first tube, yield a sample liquid suitable for use in gradient elution of a particular solute sample it is desired to analyze by liquid chromatography, and the second tube containing a further liquid whose variation of composition is the reverse of that in the first tube and is capable, on discharge from the second tube, of yielding a sample liquid for regeneration of the chromatographic column, the storage tubes being used alternately.

* * * * *